Aug. 13, 1963 O. O. DUNHAM Plant Pat. 2,274
CHRYSANTHEMUM PLANT
Filed April 2, 1962
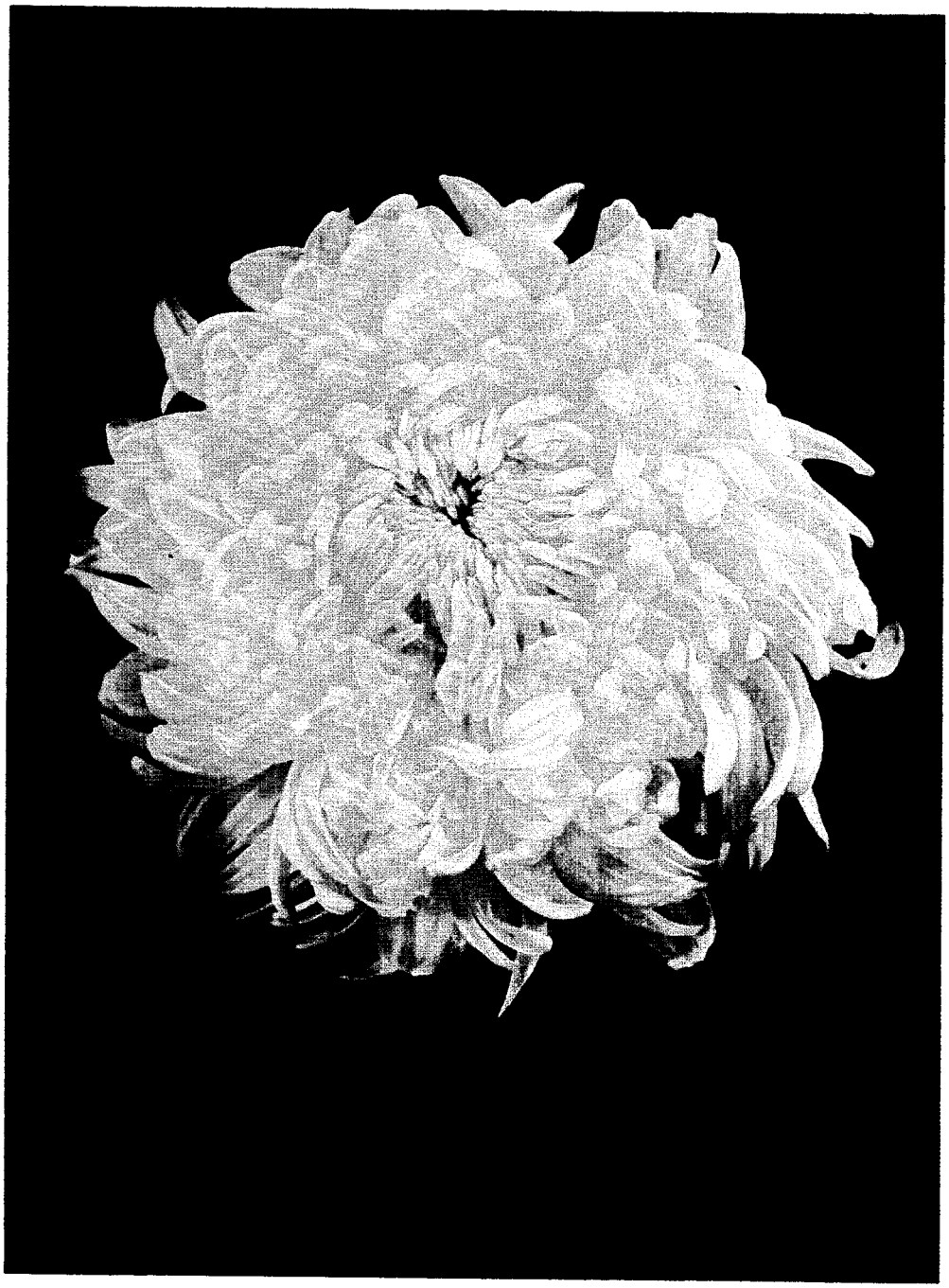
Inventor:
O. O. DUNHAM
by Robb & Robb
attorneys United States Patent Office Plant Pat. 2,274
Patented Aug. 13, 1963

2,274
CHRYSANTHEMUM PLANT

Orville O. Dunham, Niles, Mich., assignor to George J. Ball, Inc., West Chicago, Ill., a corporation of Illinois Filed Apr. 2, 1962, Ser. No. 184,616
1 Claim. (Cl. Plt.—78)

My present invention comprises a new and distinct variety of chrysanthemum plant which is the result of crossing the variety "Ermine" an unpatented variety with another unpatented variety known as "Freedom."

The object of this invention is to produce a new variety of chrysanthemum of the indicum type which derives its upright plant habit and stiff stems from one parent, the formation of the flower from the other parent and take advantage of the height of both of the parent plants to produce a tall plant likewise. The foliage habit and bloom are definite improvements over either of the parents.

I have made a study of and conducted an intensive program of development in the field of chrysanthemums and this present new variety is one of the results thereof, requiring the careful selection and cross breeding of various plants from various parent plants to take advantage of many of the characteristics of the specific parent plant and of the general strain from which the said parent plants have derived, certain of the characteristics desirably being early flowering and continuous flowering thereafter.

In consequence of the specific hybridization previously referred to I have been able to produce my present new and distinct variety of chrysanthemum characterized by the strong greenish yellow to brilliant greenish yellow color of its blooms, the large incurving formation of the blooms, the tall height of the plant and sturdy upright habit with strong stiff stems.

More specifically the blooms of my new variety are of a strong greenish yellow to brilliant greenish yellow color (Nickerson Color Fan published by the Munsell Company), the blooms having lighter outer color with a darker center. As grown in the vicinity of Niles, Michigan, in uniform culture, plants of my new variety grow to an average height of 24 to 26" and a spread of 24" in most cases.

My new variety derives a number of characteristics from both parents, but includes better characteristics than either separately primarily in the type of foliage, its habit and the blooms and differs from both of its parents and from other known varieties in many respects likewise.

Since the garden mum variety most similar in appearance to the particular plant of this invention is the variety "Illinois," an unpatented variety, a comparison of the plant of my invention therewith will show that my new variety of chrysanthemum produces larger flowers than "Illinois," the foliage is larger and the stems are longer. My new variety makes a better cut flower than "Illinois." The sturdy upright plant habit and strong stems of my new variety are derived apparently from the pollen parent "Freedom" and the incurving formation of the bloom is derived from the seed parent "Ermine." The petalage of my new variety is very double and many petals and stamens are hidden under normal conditions.

My new variety when grown in the region of Niles, Michigan, produces profuse blooms from mid-season in a continuous manner until a killing frost, the blooms being large and in clusters on each plant.

My new variety has been asexually reproduced by cuttings in the vicinity of Niles, Michigan.

My new variety has been found to retain its distinctive characteristics through successive asexual reproduction.

The accompanying drawing forming a part hereof shows a typical plant of my new variety of chrysanthemum.

The following is a detailed description of my new variety of chrysanthemum plant, the color references being to the Nickerson Color Fan published by the Munsell Color Company:

*Description*

Parentage: Seedling.
- *Seed parent.*—"Ermine" (unpatented).
- *Pollen parent.*—"Freedom" (unpatented).

Classification: Botanic—*Chrysanthemum indicum.*

*Flower*

Blooming habit: Blooms profusely from mid-season continuously until a killing frost. Observations were made in the vicinity of Niles, Michigan during October.

Bud:
- *Size.*—Large.
- *Form.*—Short with flat top.
  - The petals burn in wet weather but otherwise not affected materially by hot weather.

Color:
- *When sepals first divide.*—7.5Y 8/12.
- *When petals begin to unfurl.*—7.5Y 9/8.
- *When half blown.*—Inside of petals—7.5Y 9/8. Reverse of petals—7.5Y 9/8.
- *Sepals.*—Smooth edge.
- *Calyx.*—Shape—funnel. Size—large and broad. Aspect—smooth.
- *Peduncle.* — Length — short. Aspect — smooth. Strength—stiff. Bud opens well and is not affected by adverse conditions.

Bloom:
- *Size.*—Large. Average size when fully expanded, 5½".
- *Borne.*—In clusters, rounded and irregular.
- *Stems.*—Long, strong.
- *Form.*—When first open—high center. Permanence—retains its form to the end.
- *Petalage.*—Very double, many petals and stamens hidden. Number of petals—too numerous to count.
- *Color.*—Center of flower—10Y 8/11. Outer petals—7.5Y 9/8. Base of petals (singlet)—10Y 8/11. Inside of petals—7.5Y 9/8. Reverse of petals—5Y 9/9. General tonality from a distance—7.5Y 9/8 washed with 10Y 9/9.
- *Discoloration.*—General tonality at end of: First day—7.5Y 9/8 washed with 10Y 9/9. Second day—5Y 9/9 tinted with 5Y 8/12. Third day—2.5Y 8/12 washed with 5Y 8/12.

Petals:
- *Texture.*—Thick. Tend to rot in wet weather and burn in hot weather.
- *Appearance.*—Inside—shiny. Outside—shiny.
- *Form.*—Flat.
- *Arrangement.*—Imbricated.
- *Petaloids in center.*—Many.
- *Persistence.*—Hang on and dry.
- *Fragrance.*—None.

Genital organs:
- *Stamens, anthers.*—Small, many. Arrangement—regular around styles.
- *Stamens, filaments.*—Short.
- *Styles.*—Columnar and short, of medium thickness.
- *Ovaries.*—Protruding from calyx.

Fruit: Variety is fertile with its own pollen.
- *Form.*—Seeds protruding.
- *Aspect.*—Rough hairy.
- *Sepals.*—Recurved.

Plant:
- *Form.*—Bush.

*Growth.*—Vigorous, upright and branching.
*Height.*—26 inches.
*Spread.*—24 inches.

Foliage:

*Size.*—Large.
*Quantity.*—Abundant.
*Color.*—Under side—5GY 7/10.
*Shape.*—Lobed.
*Texture.*—Upper side—glossy.
*Ribs and veins.*—Ordinary.
*Edge.*—Undulated.
*Under side.*—Smooth.

*Stipules.*—Short and smooth.

Wood (new): Bark—smooth.

Wood (old): Bark—smooth.

I claim:

A new and distinct variety of chrysanthemum plant substantially as herein disclosed, characterized as to novelty by strong greenish yellow to brilliant greenish yellow color of its blooms, the large very double in-curved form thereof, the upright tall wide-spread shape of the plant, the strong stiff stems, and its better foliage and habit with continuous bloom.

No references cited.